United States Patent [19]

DeLuca

[11] Patent Number: 4,634,561
[45] Date of Patent: Jan. 6, 1987

[54] METHOD FOR JOINING CERAMIC COMPONENTS IN PRECISE SPATIAL RELATIONSHIP

[75] Inventor: Robert D. DeLuca, Pennington, N.J.

[73] Assignee: Johnson & Johnson Dental Products Company, East Windsor, N.J.

[21] Appl. No.: 714,668

[22] Filed: Mar. 22, 1985

[51] Int. Cl.$^4$ .................. A61C 13/20; A61C 13/08
[52] U.S. Cl. ............................ 264/17; 264/57; 264/60; 264/313; 432/258; 433/34; 433/171
[58] Field of Search .............. 264/17, 18, 57, 58, 264/60, 313; 433/24, 34, 49, 167, 171, 191; 432/258, 259, 261

[56] References Cited

U.S. PATENT DOCUMENTS

| | | | |
|---|---|---|---|
| 2,070,771 | 2/1937 | Artzt | 264/18 X |
| 2,192,902 | 3/1940 | Erdle | 264/18 |
| 2,851,728 | 9/1958 | Spalten et al. | 264/17 X |
| 3,495,333 | 2/1970 | Kuhn | 433/34 |
| 3,702,027 | 11/1972 | Marshall et al. | 433/34 |
| 4,269,595 | 5/1981 | Nemethy | 264/17 X |

FOREIGN PATENT DOCUMENTS

| | | | |
|---|---|---|---|
| 179610 | 9/1954 | Australia | 264/17 |
| 1813332 | 6/1970 | Fed. Rep. of Germany | 433/191 |
| 2064737 | 6/1981 | United Kingdom | 432/259 |
| 992983 | 1/1983 | U.S.S.R. | 432/258 |

*Primary Examiner*—Philip Anderson
*Attorney, Agent, or Firm*—Charles J. Metz

[57] ABSTRACT

Process for joining ceramic components in precise spatial relationship which comprises firing the ceramic components joined by a ceramic frit on a sagger tray having a coefficient of thermal expansion that matches that of the ceramic components.

4 Claims, 6 Drawing Figures

METHOD FOR JOINING CERAMIC COMPONENTS IN PRECISE SPATIAL RELATIONSHIP

The invention relates to a process for joining ceramic components in precise spatial relationship, and has particular applicability to the production of multiple-unit all-ceramic dental restorations.

BACKGROUND OF THE INVENTION

Multiple-unit dental restorations (i.e., bridges or pontics) have for many years been made by preparing a metal base or coping and then adding several layers of dental porcelain over the metal to simulate, as closely as possible, the appearance of natural teeth. The metal base for the bridge is usually assembled on a master cast and the individual units (teeth) are fastened together with wax containing rosin, known in the dental profession as "sticky wax". The assembly of individual units bonded together with wax is then carefully removed from the master cast and is embedded in a unitary mass of refractory cement ("soldering investment"), with only the portions of the units that are to be joined to the adjacent units exposed. After the cement has hardened, the wax is removed, as by flushing with boiling water. Next, the units are soldered together. After the soldering operation, the assembly is removed from the investment and is ready for the addition of the porcelain layers.

Recently, all-ceramic dental restorations have become commercially available. Because no metal is used in their fabrication, all-ceramic restorations can be made to more closely resemble natural dentition. Such all-ceramic dental restorations are disclosed, for instance, by Starling et al. in U.S. Pat. No. 4,265,669. Naturally, the techniques for producing an all-ceramic dental restoration must differ in some respects from those used to produce a metal-based restoration. For instance, in the preparation of an all-ceramic multiple unit restoration, the individual units cannot be soldered together as they are in a metal-based restoration. This invention is directed to a procedure that is particularly applicable for joining the individual units to each other in the production of an all-ceramic multiple unit dental restoration, although the invention is more widely applicable to the joining of all types of ceramic components that must be joined in precise spatial relationship.

BRIEF SUMMARY OF THE INVENTION

The invention provides a process for joining ceramic components in precise spatial relationship which comprises the steps of:
(a) forming a first composite comprising a plurality of individual ceramic components joined in precise spatial relationship with temporary joining means;
(b) immobilizing said first composite on a sagger with individual masses of a low temperature curing refractory cement;
(c) removing said temporary joining means while said ceramic components are maintained in said precise spatial relationship on said sagger with said refractory cement;
(d) forming a joint between each pair of adjacent ceramic components with ceramic frit to form a second composite comprising said ceramic components maintained in said precise spatial relationship on said sagger with said refractory cement, with each pair of adjacent ceramic components having a ceramic frit joint between them;
(e) firing said second composite to fuse said ceramic frit to thereby form permanent ceramic joints between said adjacent pairs of ceramic components; and
(f) removing the permanently joined ceramic components from said sagger, wherein said sagger is constructed of a material that has a coefficient of thermal expansion that matches that of the material from which said ceramic components are made.

THE PRIOR ART

The following United States Patents disclose various sagger trays that are designed for supporting porcelain-coated metal-based dental restorations during firing:
Crouse, U.S. Pat. No. 4,383,825; Tanaka, U.S. Pat. No. 4,299,567; Ouhl, U.S. Pat. No. 3,861,867; Gamberg et al., U.S. Pat. No. 4,184,840; Kikuchi et al., U.S. Pat. No. 3,885,313;

DETAILED DESCRIPTION OF THE INVENTION

Prior to carrying out the first step in the process of the invention, a model of the dental restoration is made. The dentist first prepares the teeth to receive the restoration and takes an impression. The impression is used to prepare a model of the restoration. The individual units of the restoration are all ceramic, and are preferably made using the ceramic core described in the above-mentioned Starling et al. patent, U.S. Pat. No. 4,265,669, by the technique described therein.

Figure 1:
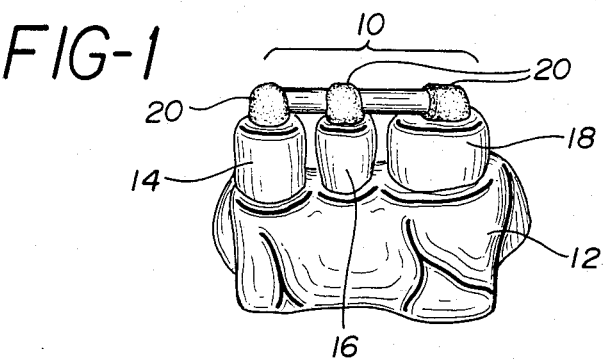
FIG. 1 is a perspective view of a three-unit, all-ceramic dental restoration on a dental mastercast, with the units being joined by sticky wax.

In FIG. 1, there is shown a three-unit, all-ceramic dental restoration 10 in place on a master cast 12, with the units 14, 16, 18 being joined by sticky wax 20. The assembly 10 is carefully removed from the cast 12 and is then placed on a sagger tray 22 that is made of a material that has the same coefficient of thermal expansion as the ceramic used in the restoration 10. (As used herein, a material having a coefficient of thermal expansion within about $0.5 \times 10^{-6}$ in/in/°C. would be considered to have the "same" coefficient of thermal expansion.) Preferably, the sagger tray 22 is made of the same material from which the ceramic cores of the restoration are made. In most cases, the sagger tray 22 will have means such as the perforations 30 shown in the drawings to provide a mechanical lock to refractory cement, which does not always adhere very well to the sagger tray 22.

Figure 2:
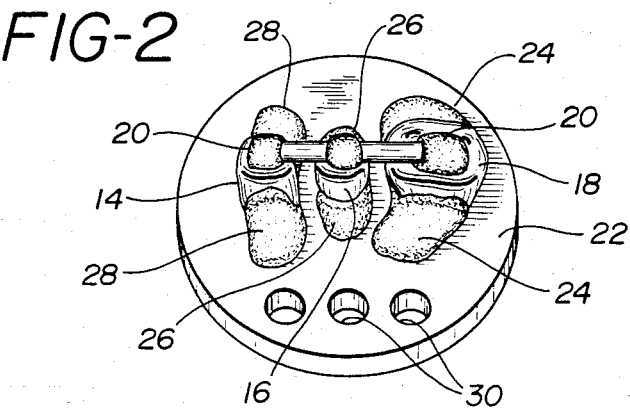
FIG. 2 is a perspective view of the dental restoration of FIG. 1 immobilized on a sagger with refractory cement.

The individual units 14, 16, 18 of the restoration are embedded in individual masses 24, 26, 28 of refractory cement on the sagger tray 22 (see FIG. 2). A typical refractory cement has the following composition:

| Component | Parts, by Weight |
|---|---|
| MgHPO$_4$ | 8 |
| (NH$_4$)H$_2$PO$_4$ | 20 |
| MgO | 20 |
| Silica (cristobalite and quartz) | 350 |

The dry ingredients are mixed with water, which forms a mixture that sets at room temperature. Other known refractory cements can also be used.

Figure 3:
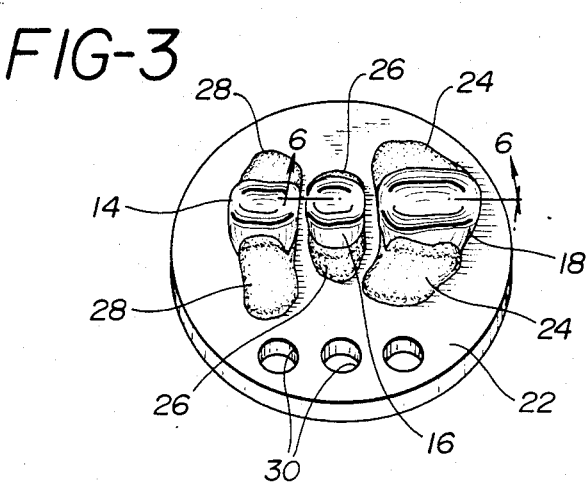
FIG. 3 is a view similar to FIG. 2, after the sticky wax joint has been removed.

The masses 24, 26, 28 of refractory cement are individual and not connected to each other so that any dimensional change that they might undergo during setting and/or firing of the tray will not significantly affect the precise spatial relationship of the three units 14, 16, 18 of the restoration 10. After the refractory cement has set, the sticky wax 20 joining the three units is removed, as by immersing the whole assembly in boiling water, which melts the wax away. FIG. 3 shows the assembly after the sticky wax has been removed.

Figure 4:
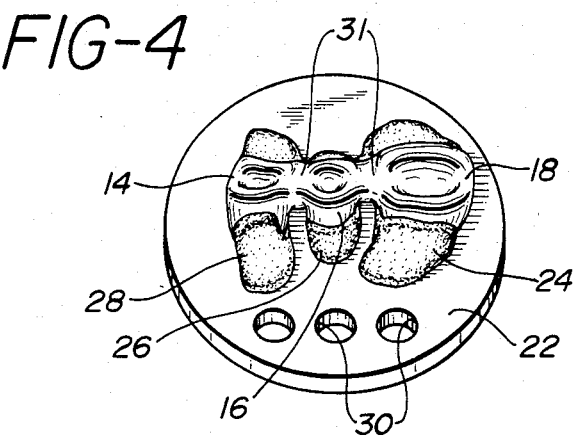
FIG. 4 is a view similar to FIG. 3, after the units have had ceramic frit added to join the units.

After the sticky wax has been removed, the units 14, 16, 18 are joined by coating the areas to be joined with an aqueous slurry of a ceramic frit 31 (see FIG. 4). A representative ceramic frit that can be used has the following overall composition:

| Component | Parts, by Weight |
|---|---|
| SiO$_2$ | 40.4 |
| Al$_2$O$_3$ | 43.0 |
| TiO$_2$ | 0.06 |
| Fe$_2$O$_3$ | 0.05 |
| MgO | 2.9 |
| CaO | 1.75 |
| Na$_2$O | 2.2 |
| K$_2$O | 2.0 |
| ZrO | 0.29 |
| BaO$_2$ | 2.10 |
| SrO | 0.06 |
| B$_2$O$_3$ | 3.92 |

The frit acts in a manner analogous to the solder used in metal-based restorations to join the units. The entire assembly is then fired to fuse the frit 31 and permanently join the units. A typical firing schedule is the following:

Pre-dry for 2 minutes at about 1150° F. under vacuum, heat from 1150° F. to 1706° F. at a rate of 100° F./minute.

In air, heat from 1706° F. to 2225° F. at a rate of 100° F./minute.

Maintain at 2225° F. for two minutes.

After the firing step, the assembly is removed from the furnace, cooled, and the restoration 10 is removed frm the sagger tray 22. At this point, the individual units 14, 16, 18 of the restoration may be coated with porcelain and glaze layers to add color and more closely simulate the appearance of natural teeth. The addition of such layers is standard in the art.

Figure 5:
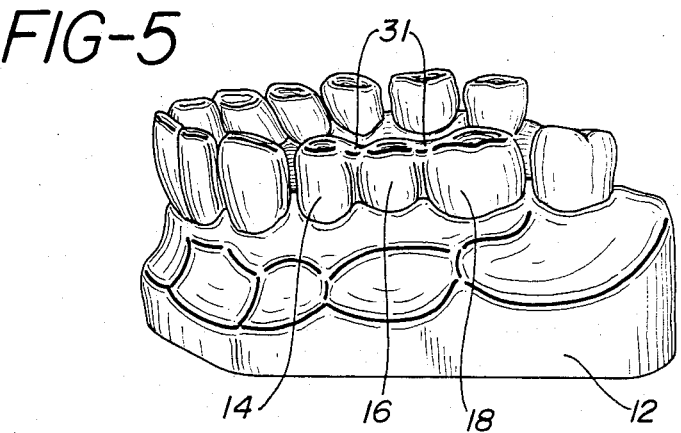
FIG. 5 is a view of the dental restoration after firing of the ceramic frit, with the restoration being replaced on the master cast.

In FIG. 5, there is shown the completed restoration as it appears after glazing and re-insertion in the master cast 12. The excellent fit of the restoration demonstrates the success of the invention in maintaining the registry of the three units in the restoration.

Figure 6:
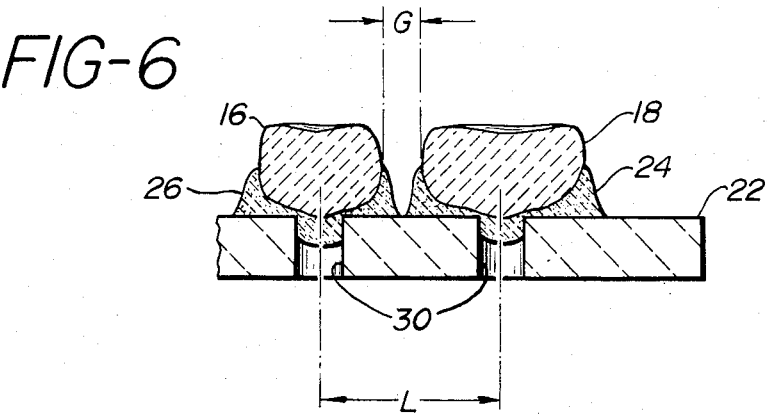
FIG. 6 is an idealized cross-sectional view taken along line 6—6 of FIG. 3.

The reason that the coefficients of thermal expansion of the individual ceramic components and the sagger tray should be the same is the following:

Referring to FIG. 6. "L" is the distance between centers of adjacent ceramic coponents and "G" is the gap distance between adjacent ceramic components. $L_O$ and $G_O$ refer to these distances at room temperature and $L_T$ and $G_T$ refer to these distances at firing temperature of the ceramic frit. If $\alpha_1$ is the coefficient of thermal expansion of the sagger tray and $\alpha_2$ is the coefficient of thermal expansion of the ceramic components, the following relationships exist:

$L_T = L_O(1+\alpha_1 \Delta T)$ and
$G_T = L_T - [(L_O - G_O)(1+\alpha_2 \Delta T)]$ wherein $\Delta T$ is the difference between the firing temperature and room temperature.

In order to minimize strain on the joint between the ceramic components, $\Delta G$ (i.e., $G_T - G_O$) should be kept as close as possible to zero in absolute numerical terms. Assuming an $\alpha_2$ of $6 \times 10^{-6}$, the resulting $\Delta G$'s for three different sagger tray materials are the following:

Assumptions:
G = 0.02 inch
L - 1 inch
1st $\alpha_1 = 6 \times 10^-$ (same material)
2nd $\alpha_1 = 15 \times 10^{-6}$ (metal)
3rd $\alpha_1 = 0.5 \times 10^{-6}$ (silica)
$\Delta T = 600° - 25° = 575°$ C.

1st $\alpha_1$:
$G_T = (1+6 \times 10^{-6} \times 575) - (1-0.02)(1+6 \times 10^6 \times 575)$
$G_T = 1.00345 - 0.98(1.00345)$
$G_T = 1.00345 - 0.983381$
$G_T = 0.020069$
$\Delta G = 0.000069$ inch 2nd $\alpha_1$:
$G_T = (1+15 \times 10^{-6} \times 575) - 0.983381$
$G_T = 1.008625 - 0.983381$
$G_T = 0.025244$
$\Delta G = 0.005244$ inch 3rd $\alpha_1$:
$G_T = (1+0.5 \times 10^{-6} \times 575) - 0.983381$
$G_T = 1.0002875 - 0.983381$
$G_T = 0.0169065$
$\Delta G = -0.0030935$ inch Thus, using typical values for L and G, it is seen that when the coefficient of thermal expansion of the sagger tray is either larger or smaller than that of the ceramic components, the $\Delta G$ is large enough to compromise the dimensions of the joined ceramic components, and possibly to fracture either the sagger tray or, more likely, the multiple unit ceramic article. For instance, when the procedure was tried using a metal sagger tray, the multiple unit shattered upon cooling to room temperature after the firing.

What is claimed is:

1. A process for joining ceramic components in precise spatial relationship, which comprises the steps of:
   (a) forming a first composite comprising a plurality of individual ceramic components joined in precise spatial relationship with temporary joining means;
   (b) immobilizing said first composite on a sagger with individual masses of a low temperature curing refractory cement;
   (c) removing said temporary joining means while said ceramic components are maintained in said precise spatial relationship on said sagger with said refractory cement;
   (d) forming a joint between each pair of adjacent ceramic components with ceramic frit to form a second composite comprising said ceramic components maintained in said precise spatial relationship on said sagger with said refractory cement, with each pair of adjacent ceramic components having a ceramic frit joint between them;

(e) firing said second composite to fuse said ceramic frit to thereby form permanent ceramic joints between said adjacent pairs of ceramic components; and (f) removing the permanently joined ceramic components from said sagger, wherein said sagger is constructed of a material that has a coefficient of thermal expansion that matches that of the material from which said ceramic components are made.

2. The process of claim 1, wherein the said individual ceramic components are individual units of a multiple unit all-ceramic dental restoration.

3. The process of claim 1, wherein said sagger and said ceramic components are made from the same material.

4. The process of claim 2, wherein said sagger and said ceramic components are made from the same material.

* * * * *